(12) United States Patent
Marano et al.

(10) Patent No.: US 11,295,836 B2
(45) Date of Patent: Apr. 5, 2022

(54) PRESERVATION OF MULTI-SERVER DATABASE FIDELITY

(71) Applicant: CERNER INNOVATION, INC., Kansas City, KS (US)

(72) Inventors: Howard T. Marano, Malvern, PA (US); Deepak Kumar Jain, Chester Springs, PA (US); Karthikeyan Sukumaran, Chester Springs, PA (US)

(73) Assignee: CERNER INNOVATION, INC., North Kansas City, MO (US)

(*) Notice: Subject to any disclaimer, the term of this patent is extended or adjusted under 35 U.S.C. 154(b) by 732 days.

(21) Appl. No.: 15/856,340

(22) Filed: Dec. 28, 2017

(65) Prior Publication Data

US 2019/0206523 A1 Jul. 4, 2019

(51) Int. Cl.
| | |
|---|---|
| *G06F 16/30* | (2019.01) |
| *G16H 10/60* | (2018.01) |
| *H04L 67/1097* | (2022.01) |
| *H04L 67/75* | (2022.01) |
| *H04L 67/1095* | (2022.01) |
| *H04L 67/1029* | (2022.01) |
| *H04L 67/1001* | (2022.01) |
| *G06F 16/27* | (2019.01) |

(52) U.S. Cl.
CPC ......... *G16H 10/60* (2018.01); *H04L 67/1029* (2013.01); *H04L 67/1095* (2013.01); *H04L 67/1097* (2013.01); *H04L 67/36* (2013.01); *G06F 16/27* (2019.01); *H04L 67/1002* (2013.01)

(58) Field of Classification Search
CPC ........ G06F 16/27; G16H 10/60; G16H 20/10; H04L 67/1002; H04L 67/1029; H04L 67/1095; H04L 67/1097; H04L 67/36
See application file for complete search history.

(56) References Cited

U.S. PATENT DOCUMENTS

| | | | |
|---|---|---|---|
| 6,665,647 B1 | 12/2003 | Haudenschild | |
| 6,898,633 B1* | 5/2005 | Lyndersay | H04L 63/08 709/217 |

(Continued)

OTHER PUBLICATIONS

"Load balancing (computing)" Wikipedia article, https://en.wikipedia.org/wiki/Load_balancing_(computing), accessed Dec. 21, 2017, 8 pages.

(Continued)

*Primary Examiner* — Mahesh H Dwivedi
(74) *Attorney, Agent, or Firm* — Shook, Hardy & Bacon LLP (57) ABSTRACT

Methods, systems, and computer-readable media are provided for the automated preservation and downtime mitigation of server-based databases and applications. Read and write operations intended for a database may be communicated to a load balancer. The load balancer may direct the operations to a primary server and/or a backup server. Further, during periods of primary server downtime, write-based tasks, operations, and/or requests of remote applications may be deactivated by the load balancer. Additionally, the load balancer may prevent corruption of backup databases from coming out of sync, and/or unexpected, undesirable, or unwanted data modification by deactivating, denying, locking, or otherwise preventing the write operations of the backup server.

13 Claims, 5 Drawing Sheets

(56) References Cited

U.S. PATENT DOCUMENTS

| | | | |
|---|---|---|---|
| 7,441,046 B2 | 10/2008 | Kaehn et al. | |
| 7,984,126 B2 | 7/2011 | McBride | |
| 8,775,624 B2 | 7/2014 | McNair | |
| 2003/0208381 A1* | 11/2003 | Walter | G16H 10/60 705/3 |
| 2004/0073831 A1* | 4/2004 | Yanai | G06F 3/0689 714/6.32 |
| 2006/0053333 A1* | 3/2006 | Uhlmann | G06F 11/1464 714/2 |
| 2006/0229918 A1* | 10/2006 | Fotsch | G06Q 40/08 705/3 |
| 2007/0192137 A1* | 8/2007 | Ombrellaro | G06Q 10/10 705/2 |
| 2007/0203910 A1* | 8/2007 | Ferguson | G06F 16/27 |
| 2009/0235067 A1* | 9/2009 | Miller | H04L 63/0823 713/151 |
| 2010/0036952 A1* | 2/2010 | Hazlewood | G06F 15/173 709/226 |
| 2010/0242082 A1* | 9/2010 | Keene | H04L 63/14 726/1 |
| 2010/0262435 A1* | 10/2010 | Smith | G06Q 50/24 705/3 |
| 2011/0286594 A1* | 11/2011 | Resch | G06F 11/10 380/46 |
| 2012/0059668 A1* | 3/2012 | Baldock | G16H 10/60 705/3 |
| 2015/0150086 A1* | 5/2015 | Clark | G16H 10/60 726/3 |
| 2015/0301910 A1* | 10/2015 | Sathyanarayana | G06F 11/2041 714/4.11 |
| 2016/0034357 A1* | 2/2016 | Anglin | G06F 11/203 714/4.11 |
| 2016/0092532 A1* | 3/2016 | Jia | H04L 67/1002 707/621 |
| 2016/0140141 A1* | 5/2016 | Darcy | H04L 67/1023 707/827 |
| 2017/0300634 A1* | 10/2017 | Chiang | G16H 10/60 |
| 2018/0096068 A1* | 4/2018 | Venkataramanappa | G06F 11/1469 |
| 2018/0239677 A1* | 8/2018 | Chen | G06F 11/2094 |
| 2019/0146891 A1* | 5/2019 | Ben Dayan | G06F 11/3485 714/4.11 |

OTHER PUBLICATIONS

"Failover" Wikipedia article, https://en.wikipedia.org/wiki/Failover, accessed Dec. 21, 2017, 2 pages.

\* cited by examiner

PRESERVATION OF MULTI-SERVER DATABASE FIDELITY

BACKGROUND

Hospitals, clinics, care facilities, surgicenters (surgical centers), and the like depend on continuous and uninterrupted access to electronic health records (EHRs). Clinicians access EHRs to, for example, document patient care, examine patient histories, review medications, prescribe medications, enter orders for a patient, check a status of an order, etc. EHRs are relied on to verify patient identities, diagnoses, allergies, laboratory results, and so on. EHRs are instrumental in billing, regulatory compliance, and quality assurance. As such, EHR reliability is a fundamental necessity of modern healthcare operations.

However, the servers and/or database clusters that store EHR systems (including the EHR application, the EHR patient records, facility data, billing information, care plan data, and so on) occasionally must be taken offline to, for example, upgrade server hardware, upgrade computer readable storage, upgrade to newer versions of EHR applications, and so on. In some cases these events, or other similar events, require destructive data migration that are incompatible with the older version of the EHR application. Further, the likelihood of unpredictable events affecting server or database clusters such as power surges, data corruption, fires, and the like can be minimized with careful planning but cannot be rendered impossible.

Generally, a hospital will chart on paper records when an EHR system is down, and/or store information on local computers until the EHR system can be restored. However, options for accessing patient data not already stored locally on the computer a health care provider are currently very limited. Some currently used solutions involve periodically dumping the data stored in the entire EHR system into portable document files (PDF). However, this solution is generally incompatible with, or severely hinders, the standard operating procedures of the healthcare system. For example, modern patient-medication verification procedures generally rely on multiple scans of the medication, a patient identifier (such as a wrist band with a barcode, RFID, and/or some other computer readable indicator), and potentially a delivery instrument (intravenous pump). Usually, the EHR system application and EHR database cluster handles this process automatically by receiving the scans, confirming the identity of the medication, confirming the identity of the patient, confirming the medication was prescribed to the patient, confirming the dosage, verifying the patient is not allergic to the medication and/or that there are no medication counter-indications, etc. PDFs, while useful, are incompatible with this process. Further, as EHR systems become more reliable the downtime processes are used less frequently. Because of this, when there is a downtime the alternative procedures are unfamiliar to the staff and untested for long periods of time. These problems can impact patient care by delaying it or making the wrong decisions due to the lack information on the patient.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

Aspects described herein relate to systems, methods, and devices that facilitate the automated preservation and downtime mitigation of server-based databases and applications, such as the majority of electronic health records systems. Further, some aspects relate to preventing modification of data of backup EHR databases during a period of primary server migration and/or downtime by deactivating write-based tasks, operations, and/or requests of the remote EHR system applications. Some aspects relate to preventing modification of data of backup EHR databases by deactivating, denying, locking, or otherwise preventing the write operations of the backup server itself.

BRIEF DESCRIPTION OF THE DRAWINGS

Embodiments are described in detail below with reference to the attached drawings figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The present application is directed, in part, to switching EHR systems, such as from a primary EHR system to a backup EHR system. In some respects, the present application relates to detecting and responding to planned and/or unplanned primary EHR system downtime while, at least partially, minimizing the risk of the EHR system coming out of sync, and/or unexpected, undesirable, or unwanted data modification. Further, some aspects relate to preventing backup EHR databases from coming out of sync, and/or unexpected, undesirable, or unwanted data modification during a period of primary server downtime by deactivating write-based tasks, operations, and/or requests of the remote EHR system applications. Some aspects relate to preventing corruption of backup EHR databases by deactivating, denying, locking, or otherwise preventing write operations of the backup server itself.

As such a first aspect is directed to a system for automatic preservation of a medical database. The system may include a first server, a second server, and a remote access hub (e.g., a load balancer). The first server is for: receiving, from the remote access hub, one or more requests to access patient information; and, providing a read or a write access to the patient information stored in a communicatively coupled first database in response to receiving the one or more requests to access patient information. The second server is for: receiving patient information requests from the remote access hub; providing patient information stored in a communicatively coupled second database in response to receiving patient information requests; receiving backup requests from the remote access hub; and, in response to receiving the backup requests, storing the patient information stored in the first database in a communicatively coupled second database. The remote access hub (load balancer) is for: receiving the one or more requests from a plurality of remote user devices, detecting a status of the first server, and communicating a read request to the second server in response to detecting that the status of the first server is off-line.

A second aspect is direct to a computer implemented method for automatic medical database preservation. The method includes communicating, by a load balancer configured to monitor a status of a first server and a second server, read and write requests for a health records database communicatively coupled to the first server, the second server communicatively coupled to a backup health records database. Further, the method includes requesting, by the load balancer, a first status check of the first server, the status check indicating the operational performance of the first server. The load balancer may receive a response to the first status check from the first server. Based on the response to the first status check the load balancer may determine a category of the first status check response from the first server, the categories comprising a negative category and a positive category. In response to the load balancer determining that the status check response is within the negative category, the method: 1) disables communication of read and write requests to the health records database; 2) deactivates write operations of the backup health records database; and, 3) directs read requests intended for the health records database to the backup health records database through the second server.

A third aspect is directed to computer readable media storing computer readable instructions that when provided to at least one processor cause the at least one processor to perform actions. The instructions may cause the processor to establish at least one channel of communication between a processor and a first server configured to provide read and write access to a plurality of remote user devices. Further, the instructions establish at least one channel of communication between the at least one processor and a second server configured to provide write access to the first server and read access to the plurality of remote user devices. Further, the instructions may provide the plurality of remote user devices read and write access to the first server. At predetermined intervals, the load balancer may provide the first server write access to the second server such that the second server undergoes an automatic back up of the first server. Further, the instructions may cause the processor of the load balancer to detect whether the first server is non-responsive to the plurality of remote user devices. In response to detecting that the first server is non-responsive to the plurality of remote user devices, the instructions may cause the load balancer to redirect read access for the plurality of remote user devices from the first server to the second server and denying write access to the first server. Further, the instructions may continue to allow the load balancer to receive a write access request and provide a notification of a non-responsive status of the first server to at least one of the plurality of remote user devices requesting write access. The instructions may also provide read access to the second server to the at least one of the plurality of remote user devices requesting write access.

Figure 1:
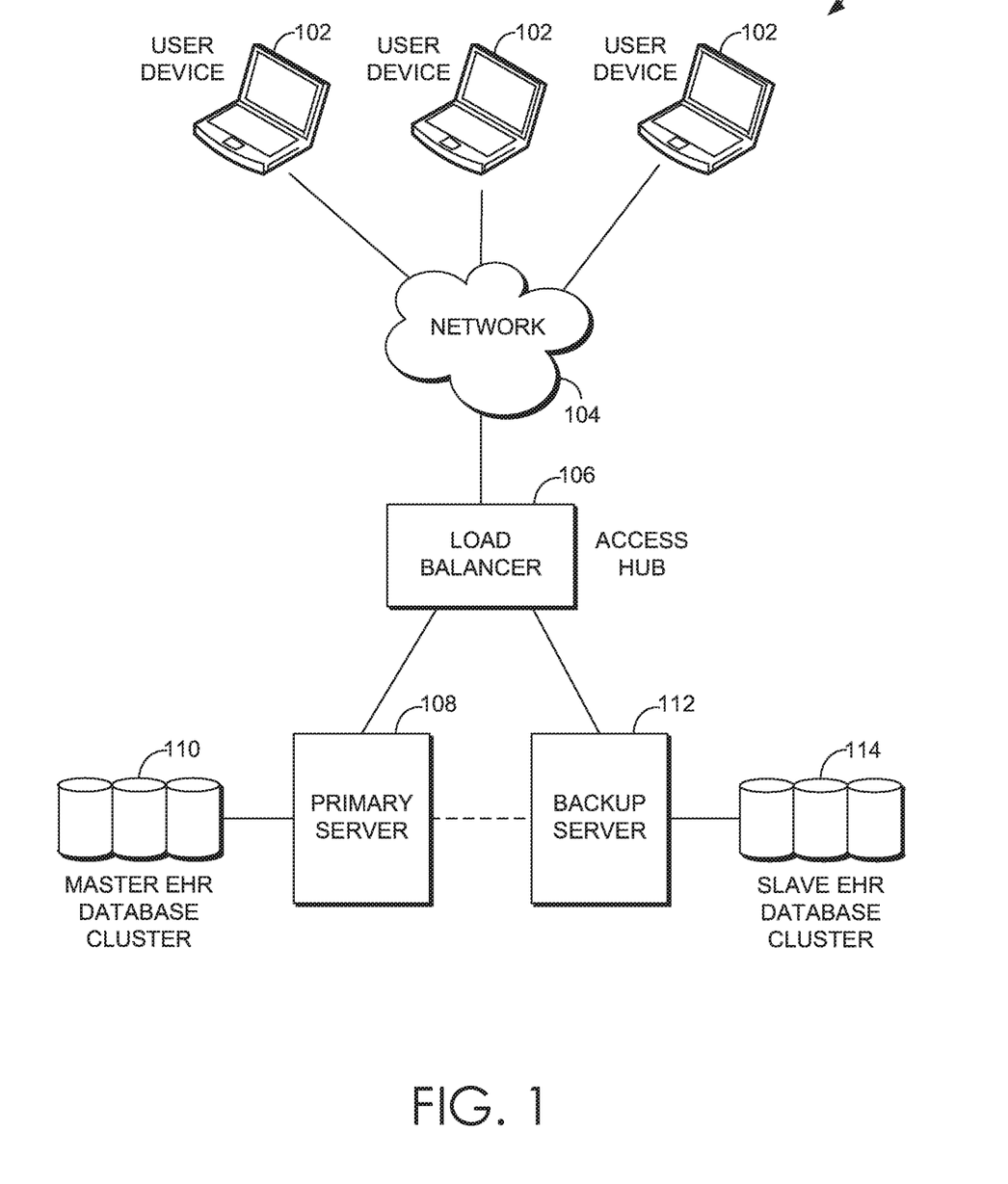
FIG. 1 is a block diagram of an exemplary computing environment suitable to implement embodiments of the present invention.

Referring now to FIG. 1, an exemplary distributed computing environment 100 is depicted on which embodiments of the present invention may be implemented. It will be understood and appreciated by those of ordinary skill in the art that the illustrated environment 100 is merely an example of one suitable computing environment and is not intended to suggest any limitation as to the scope of use or functionality of the invention. Neither should the environment 100 be interpreted as necessarily having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes user devices, such as user device 102, a network 104, a load balancer 106, a primary server 108 communicatively coupled with a master EHR database cluster 110, and a backup server 112 communicatively coupled with a slave EHR database 114.

The user devices 102 may be personal computers, network PCs, peer devices, or the like, and may include some or all of the components described above in relation to the server 108. The devices can be personal digital assistants, smartphones, or other like devices. In some embodiments, user device 102 is a general purpose computing device operating purpose built software. For instance, user device 102 may operate client applications, such as applications which access EHR systems (remote EHR system applications) through network 104. In some embodiments of environment 100 user devices 102 comprise both purpose built devices and general purpose devices operating purpose built software. User interactions with the user devices 102 create information requests that are transmitted on network 104. The user may use an input device connected to user device 102 to interact with a graphical user interface associated with the remote EHR system application which allows the user to access a hospital, clinic, healthcare system, or the like's EHR system. For instance, the user may be an in-take nurse who is registering a patient. The nurse may access the remote EHR system application and then search for the patient's name. At least one information request is generated by the nurse's user device to query the EHR database for patients with similar names. The information request(s) are transmitted to the load balancer 106. In one embodiment, the information requests created by the user devices 102 are packets of digital information that includes an internet protocol (IP) address of the user device 102. Further, the information requests may include an IP address associated with the load balancer 106.

Exemplary computer networks, such as network 104, may include, without limitation, local area networks (LANs) and/or wide area networks (WANs). Such networking environments are commonplace in offices, enterprise-wide computer networks, intranets, and the Internet. When utilized in a WAN networking environment, the server 108 may include a modem or other means for establishing communications over the WAN, such as the Internet. In a networked environment, program modules or portions thereof may be stored in the load balancer 106, primary server 108, in the backup server 112, in the master EHR database cluster 110, in the slave EHR database cluster 114, and/or on any of the user devices 102. For example, and not by way of limitation, various application programs may reside on the memory associated with any one or more of the user devices 102, load balancer 106, in the primary server 108, in the backup server 112, in the master EHR database cluster 110, and/or in the slave EHR database cluster 114. It will be appreciated by those of ordinary skill in the art that the network connections shown are exemplary and other means of establishing a communications link between the computers (e.g., server 108 and remote computers such as user device 102) may be utilized.

Components of the primary server 108 and/or backup server 112 may include, without limitation, a processing unit, internal system memory, and a suitable system bus for coupling various system components, including database clusters 110 and 114 respectively. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus. Generally the servers (primary server 108 and backup server 112), process the information requests communicated to the servers and transmit the response to the load balancer 106. In some embodiments, the response may be returned from the servers without traversing the load balancer 106.

Master EHR database cluster 110 generally includes one or more databases of patient information (lab results, medication, allergies, demographics, and so on), facility information (room location, equipment information, and so on), policy information (hospital standards, policies, procedures, and so on), billing information (insurance contracts, physician rates, and so on), and/or other information related to the operation of the healthcare facility. Further, the master EHR database cluster 110 may be a relational database that is maintained by a software infrastructure such as a structured query language (SQL) or the like. Additionally, the Master EHR database cluster 110 may refer to one or more instances of the databases. The Master EHR database cluster 110 may interface with an EHR system application that provides user device 102 remote access to the master EHR database cluster 110. Further, data may be written to or read from the master EHR database cluster 110 through the EHR system application and/or remote EHR system applications (such as those run on user device 102).

Slave EHR database cluster 114, similar to master EHR database cluster 110, generally includes one or more databases of patient information (lab results, medication, allergies, demographics, and so on), facility information (room location, equipment information, and so on), policy information (hospital standards, policies, procedures, and so on), billing information (insurance contracts, physician rates, and so on), and/or other information related to the operation of the healthcare facility. Further, the slave EHR database cluster 114 may be a relational database that is maintained by software infrastructure such as SQL or the like. The slave EHR database cluster 114, may interface with an EHR system application. Further, data may be written to the slave EHR database cluster 114 by the load balancer 106 and/or the master EHR database cluster 110. In an embodiment, the data is written to the slave EHR database cluster 114 by the master EHR database cluster 110. Data may be read from the slave EHR database cluster 114 by the EHR system application and/or remote EHR system applications (such as those run on user device 102).

In operation, a user may enter commands and information into the server, such as primary server 108 and/or backup server 112, or convey the commands and information to the server via one or more of the user device 102 through input devices, such as a keyboard, a pointing device (commonly referred to as a mouse), a trackball, or a touch pad. Other input devices may include, without limitation, microphones, satellite dishes, scanners, or the like. Commands and information may be sent directly and/or indirectly from a remote user device to a load balancer.

Figure 2:
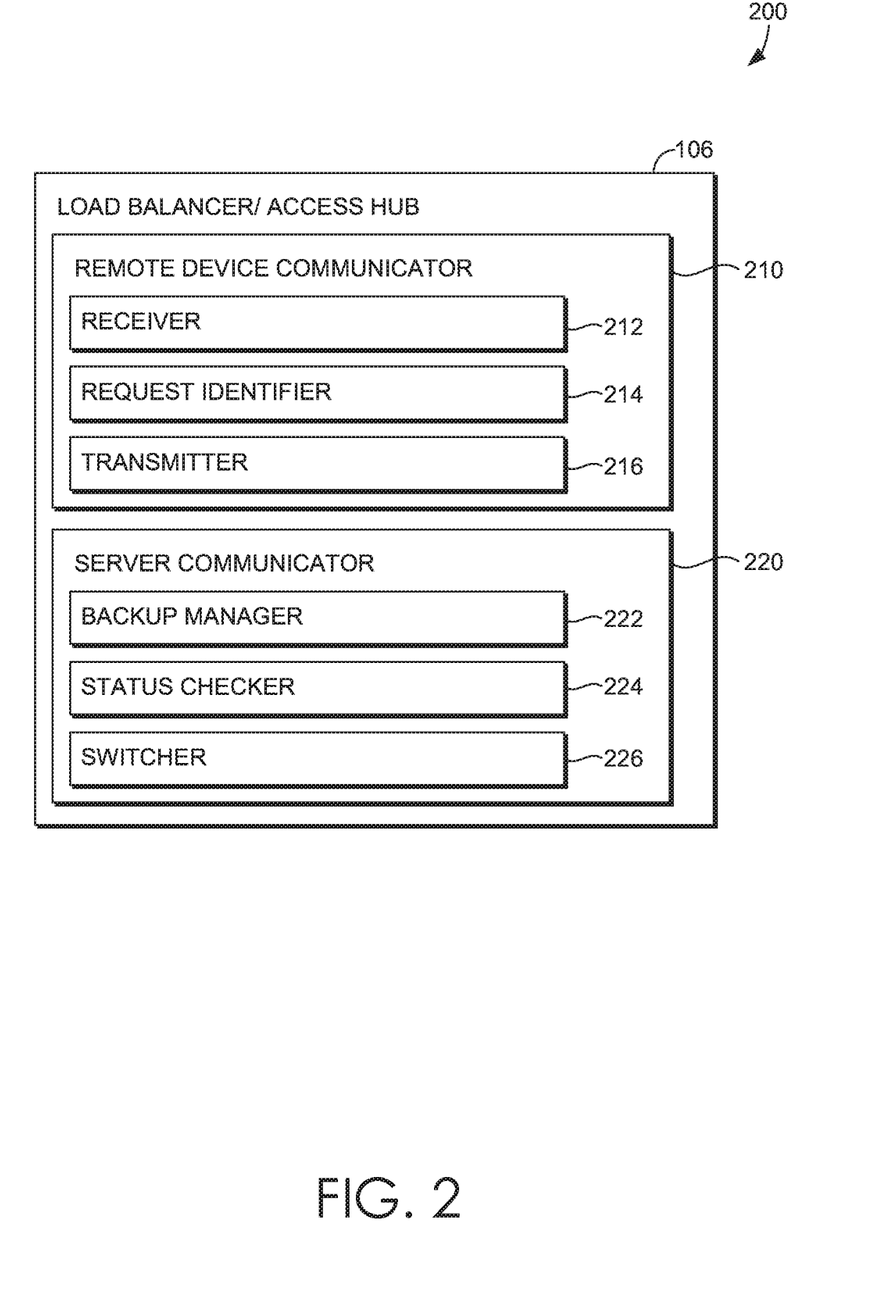
FIG. 2 is a block diagram of an exemplary system, in accordance with an embodiment of the present invention.

Turning to FIG. 2, an exemplary system 200 with which embodiments of the present invention may be implemented is depicted. It will be understood and appreciated by those of ordinary skill in the art that the illustrated medical information computing system 200 is merely an example of one suitable computing environment and is not intended to suggest any limitation as to the scope of use or functionality of the invention. Neither should the system 200 be interpreted as necessarily having any dependency or requirement relating to any single component or combination of components illustrated therein.

Generally, a load balancer 106 may act as an automated or semi-automated network traffic control system. For example, the load balancer 106 may receive a request to read and/or write information in a patient's EHR stored in an EHR system. The load balancer 106 may determine that the primary EHR system, such as an EHR system accessible to primary server 108, is online and operational. The load balancer 106 may allow the request to continue to, and/or direct the request to, the primary EHR system. Alternatively, the load balancer 106 may determine that the primary EHR system is offline and/or non-operational. In such a case, the load balancer 106 may direct requests to read information stored in a backup EHR system, such as an EHR system accessible to backup server 112. Further, load balancer 106 may deny, block, prevent, deactivate, and/or otherwise disable requests to write information to the backup EHR system.

Some embodiments of load balancer 106 comprise a remote device communicator 210 and a server communicator 220. Generally, remote device communicator 210 processes and/or monitors incoming requests from remote user devices, such as user device 102 of FIG. 1. For example, the remote device communicator 210 may receive a request to read and/or write information in a patient's EHR stored in a database cluster of an EHR system. The remote device communicator 210 may log a unique identifier associated with the source of the request, such as a media access control (MAC) address, device serial number, internet protocol (IP) address, and/or the like. Additionally, the remote device communicator 210 may determine whether the request is a read request or a write request. For example the remote device communicator 210 may identify if the request is to create, update, delete, or view data in the EHR system. Further, the remote device communicator 210 may process and/or monitor outgoing responses bound for remote user devices, such as user device 102. As such, some embodiments of the application include the remote device communicator 210 comprising a receiver 212, a request identifier 214, and/or a transmitter 216.

Generally, receiver 212 receives incoming information requests from the user devices 102 and/or responses to information requests from the primary server and/or backup server. The receiver 212 may parse packets of the incoming information requests to identify the source by, for example, identifying an IP address and/or MAC address of the sending device. Further, the receiver 212 may communicate the information requests to other components or subcomponents of the load balancer 106. For instance the receiver 212 may act as a pass through to the transmitter 216 for some responses received from the primary server 108 and/or the backup server 112. Additionally, as discussed below, the receiver 212 may distribute portions or all of the information packet that includes the information requests to the request identifier 214, the server communicator 220 and/or its respective subcomponents such as the backup manager 222, the status checker 224, and the switcher 226.

Request identifier 214 generally determines whether the incoming request is a read or write request. In some embodiments, request identifier 214 parses the information request and determines whether the packet of data associated with the request includes data intended to be written in an EHR database or includes a request for information already present in the EHR database.

Generally, transmitter 216 sends information requests to the primary server and/or the backup server and/or responses to information requests to the user devices 102. For instance, the transmitter 216 may assemble packets of information intended to communication to other members of the system. The transmitter 216 may generate source address information (for example the IP address and/or MAC address of the load balancer), and destination address information (for example the IP address and/or MAC address of the primary server 108, the backup server 112, and/or a specific user device, such as user device 102).

Server communicator 220 generally processes, manages, and monitors server status and server-to-server communications. For example, the server communicator 220 may identify and connect with a primary server and/or identify and connect with a secondary server. In some embodiments, the server communicator 220 manages the connection process by providing IP addresses associated with the primary and backup servers to the remote device communicator 210.

Backup manager 222 generally generates commands for transmission to the primary server 108 and/or backup server 112 to trigger and/or facilitate the automatic backup of the master EHR database cluster 110 to the slave EHR database cluster 114. For example, the backup manager 222, may access a digital log of write requests communicated by the load balancer 106 to the primary server 108. Based on the digital log of write requests, a set of updated, modified, edited, or otherwise altered health records (or other data) stored in the master EHR database cluster 110 can be identified by the load balancer. The load balancer 106 may send a request for the set of updated health records (or other data). The request may be a packet of information, including the identification of the set of altered health records (or other data) to the primary server 108. The packet of information may also include the IP and/or MAC address of the backup server 112. In response, the primary server 108 may access the updated health records (or other data) stored in the master EHR database 110. Further, the primary server 108 may communicate the updated health records (or other data) to the load balancer 106 which may forward the updated health records (or other data) set and a command to write the data to the backup server 112 for storage in the slave database cluster 114. Additionally, and/or alternatively, the primary server 108 may communicate the updated health records (or other data) directly to the backup server 112 for storage in the slave database cluster 114.

Status checker 224 generates status check requests for the primary server 108 and/or backup server 112 and analyzes the results of status checks when they are received from the servers. For example, the analysis may comprise a comparison of the diagnostic process to a predetermined set of rules stored in the memory of the load balancer 106. It will be understood by those skilled in the art that the rules may vary by the requirements and/or tolerances of the specific database administrator and the policies, standards, and procedures of the hospital, healthcare facility, clinic, and so on. However, in general, at least three conclusions may be determined based on the analysis of the diagnostic process: 1) the primary server and the master EHR database cluster are operational; 2) the primary server is operational but the master EHR database cluster is nonoperational; and/or, 3) the primary server is nonoperational. Further, the status checker 224 may automatically determine that absence of a response from the primary server within a predetermined duration after the load balancer requests the status check is an indication that the first server is nonoperational and/or offline.

Switcher 226 generally triggers the read only mode protocol in response to the load balancer 106 detecting that the primary server 108 and/or the master EHR database cluster 110 is offline, nonresponsive, nonoperational, or otherwise not functioning properly. For instance the switcher 226 may instruct the transmitting component to communicate read requests received from user device(s) 102 to the IP address and/or MAC address associated with the backup server 112. Further, when activated, the switcher 226 may generate a predetermined packet for communication to user device 102 including a command to deactivate any and all tasks that include a write request available within a remote EHR system application operating on the user device 102. In other words, in an embodiment, the switcher 226 disables any and/or all tasks accessible in the remote EHR system application that include at least one information request that writes (e.g. attempts to write) information to an EHR database cluster. Further, the switcher 226 may generate and communicate a predetermined disabling packet to the backup server 112, which deactivates, disables, locks, or otherwise suspends any and/or all write operations. Switcher 226 may include an application scanning protocol which identifies each task available within the EHR system application and the operations associated with each task. For instance, adding a note to a patient's EHR may be a task;

opening a patient's EHR may be a task, entering medication information may be a task, creating discharge orders may be a task, creating an insurance bill may be a task, and so on. Each task may comprise multiple information requests. For example, the task of adding a note may comprise a read operation associated with identifying the most recent encounter identifier used in the global EHR system; a write operation associated with creating an new encounter identifier; a write operation associated with assigning the new encounter identifier to a patient; a read operation for populating the GUI with previous notes associated with the patient for reference; and so on. It will be understood by those skilled in the art that this is merely illustrative and not meant to limit the scope of the embodiments disclosed herein. Further, it will be understood that each task may include fewer, more, and/or different information requests and the operations associated with each information request identified above may comprise multiple read and/or write operations.

Figure 3:
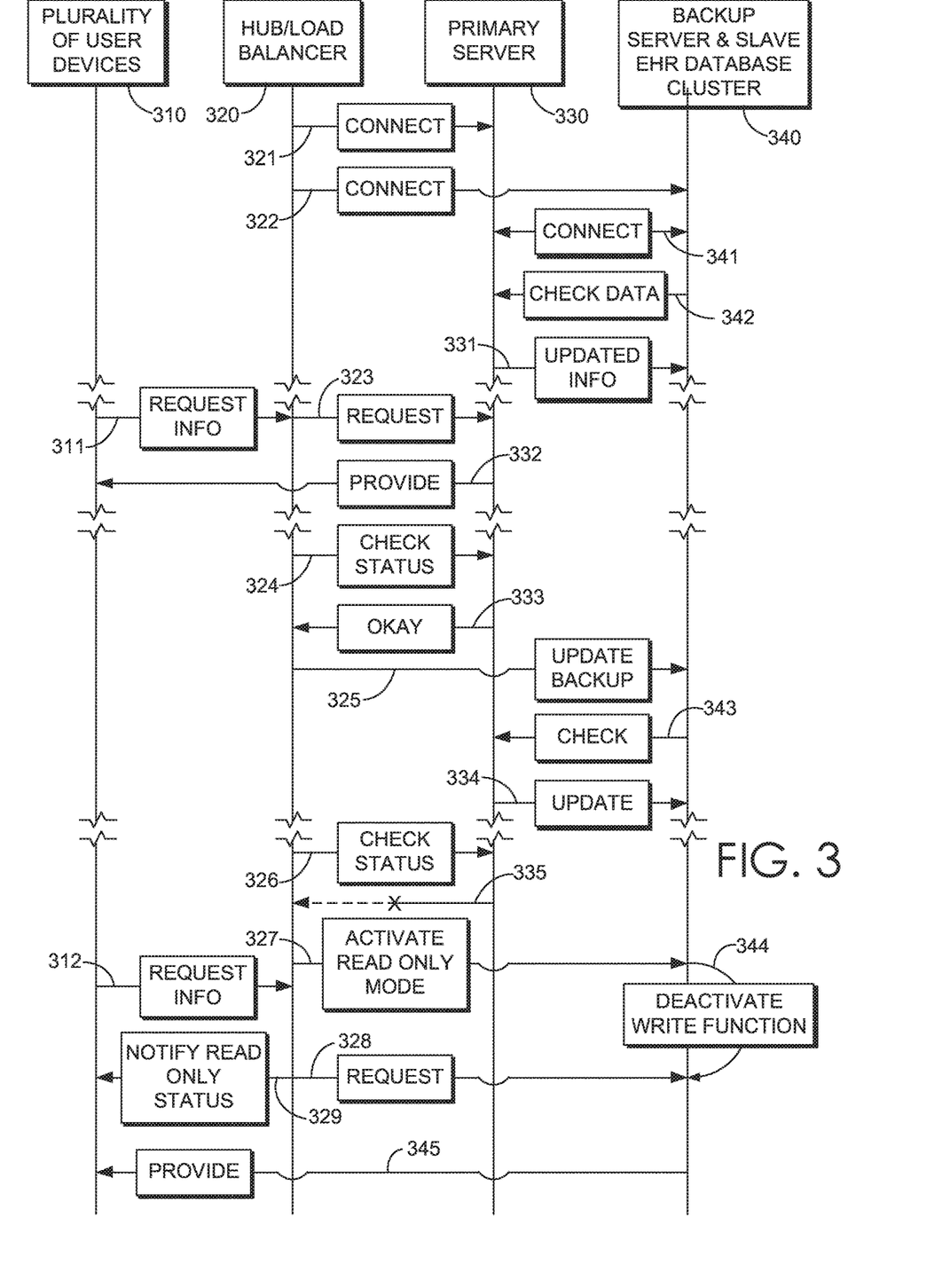
FIG. 3 is an exemplary activity diagram, in accordance with an embodiment of the present invention.

FIG. 3 illustrates an activity diagram 300 for connecting a load balancer 320 with a primary server 330 and a backup server 340; initializing a master-slave relationship between the primary server 330 and the backup server 340; communicating requests from a user device 310 through the load balancer 320 to the primary server 330; checking the status of the primary server 330 and the load balancer 320; triggering a backup of the primary server 330 to the backup server 340; and, responding to detected primary server 330 outages by activating the contingency protocol of the backup server 340. Although depicted as an activity diagram, it will be understood by those skilled in the art that activity diagram 300 also depicts several exemplary methods suitable to facilitate automatic server-based medical database preservation.

Activity diagram 300 begins at step 321 and/or step 322 when the load balancer 320 establishes a communication channel between the load balancer 320 and the primary server 330 and/or the backup server 340. In some embodiments, the primary server 330 and/or the backup server 340 may initiate the communication channel between the server(s) and the load balancer 320. For example, the primary server 330 and/or the backup server 340 may send a packet of data, which includes the IP address and/or MAC address of the server, to the load balancer 320. As another example, the load balancer 320 may send a packet of data, which includes the IP address and/or MAC address of the load balancer 320, to the primary server 330 and/or the backup server 340. It will be understood by those skilled in the art that any handshake, initialization, or setup protocol may be used to establish the communication channel between the load balancer 320 and the primary server 330 and/or the backup server 340.

In some embodiments of step 322, the load balancer 320 may further send a command to the backup server 340 to establish a communication channel between the primary server 330 and the backup server 340. For example, at step 341 the backup server 340 may send a packet of data which includes the IP address and/or MAC address of the backup server 340 to the primary server 330. In some embodiments of step 322, the load balancer 320 may command the backup server 340 to establish a communication channel between the primary server 330 and the backup server 340 through a server communication component of the load balancer 320. In an embodiment, once the communication channels are established between the load balancer 320, primary server 330, and the backup server 340, the method proceeds to step 342.

At step 342, the backup server 340 checks with the primary server 330 for any new, modified, changed, deleted, or otherwise altered data structures and/or information. For example, in an embodiment, the backup server 340 requests access to a database accessible to the primary server 330, such as a master EHR database cluster 110 of FIG. 1. Differences between the data accessible to the backup server 340 and the primary server 330 are identified. In step 331, the identified differences are communicated from the primary server 330 to the backup server 340. For example, the primary server 330 communicates data contained in the master EHR database cluster, such as master database cluster 110, to the backup server 340. The primary server 330 may send a series of write commands to the backup server 340 to copy the data currently stored in the master EHR database cluster to the slave database cluster. In an embodiment, the identified differences are communicated to the backup server 340 through the load balancer 320. The data (e.g., records), including any and/or all related data structures, may be copied from the primary server 330 to the backup server 340.

At step 311 a user device 310 communicates an information request to load balancer 320. The information request may be a read or a write request intended to read or write information in the EHR system. The load balancer 320 may receive the request and parse the request to identify whether it is a read or a write request.

At step 323, the information request is communicated from the load balancer 320 to the primary server 330. In the event that the information request is a read request, the primary server 330 provides the requested information directly or indirectly (through the load balancer 320) back to the user device 310. For example, primary server 330 may access a patient's lab results, insurance information, allergy information, room assignment, primary care physician, and/or any other data stored in a master EHR database cluster, such as master EHR database cluster 110 of FIG. 1. The information is provided to the user device 310 for presentation in the remote EHR system application. In the event that the information request is a write request, the primary server 330 writes the information to the master EHR database cluster, such as master EHR database cluster 110. For example, primary server 330 may write a patient's lab results, insurance information, allergy information, room assignment, primary care physician, and/or any other data intended to be stored in the EHR system. Additionally, the write request may modify the information already stored. For example, the primary server 330 may modify (e.g. update, delete, and/or the like) a patient's lab results, insurance information, allergy information, room assignment, primary care physician, and/or any other data already stored in the EHR system. The primary server 330 may confirm that the write request is executed by providing a confirmation to the user device 310.

At step 324, the load balancer 320 checks the status of the primary server 330. The status check may comprise communicating a predetermined data packet to the primary server 330. In an embodiment, in response to receiving the status check, the primary server 330 initializes a diagnostic process to test the performance or integrity of the primary server 330 and/or the master EHR database cluster accessible to (i.e. communicatively coupled with and/or stored in the memory of) the primary server 330. The results of the diagnostic process may be communicated back to the load balancer 320 for analysis. For instance, the diagnostic process may indicate that: the primary server 330 is operational; the primary server 330 is operational but the EHR database cluster is nonoperational; or, the primary server 330 is nonoperational. Further, in an embodiment, the absence of a response from the primary server 330 within a predetermined period of time is automatically interpreted by the load balancer 320 as an indication that the primary server 330 is nonoperational.

At step 333, the primary server 330 may respond to the status check of step 324 with an indication that the primary server 330 is operational. Alternatively, at step 333, the results of the diagnostic process of the primary server 330 may be analyzed. The determination is made whether the primary server 330 (and/or master EHR database cluster) is operational or nonoperational. At step 325, in response to determining that the primary server 330 (and/or master EHR database cluster) is operational, the load balancer 320 may communicate a predetermined data packet that causes the backup server 340 to update the information stored in the slave EHR database cluster. In other words, in an embodiment, after a load balancer determines that the primary server and master EHR database cluster are operational, the load balancer initiates an automatic backup of the master EHR database cluster to the slave EHR database cluster. Initiation may comprise sending a predetermined packet of data to the slave EHR database cluster.

In response to receiving the predetermined packet, the backup server 340 may check the primary server 330 to identify any information and/or data structures that have changed since a previous backup (if any exist) was initiated. Additionally, and/or alternatively, the load balancer 320 may communicate a packet of data comprising a digital log of write requests identified by a request identification component of the load balancer, such as request identifier 214 from FIG. 2, since the previous backup (if any exist) was initiated by the load balancer 320. In an embodiment, the digital log of write requests provides the backup server 340 and/or the primary server 330 a set of data that has been modified since the previous backup.

At step 343, the backup server 340 checks for changes in the data stored in the primary server 330. In an embodiment, an audit trail recorded by the EHR system application stored in the EHR database cluster 110 facilitates identification of changes in the data stored in the primary server 330. For instance the backup server 340 may communicate the time stamp associated with the previous backup to the primary server 330. The primary server 330 may compare the time stamp with the audit trail and determine which data has been modified. The modified set of data may then be communicated from the primary server 330 to the backup server 340 at step 334.

At step 326, the load balancer may communicate a status check to the primary server 330, similar to step 324. However, at step 335: 1) the primary server 330 indicates that the primary server 330 is operational but the EHR database cluster is nonoperational; 2) the primary server 330 indicates that the primary server 330 is nonoperational; or, 3) the primary server 330 fails to respond to the status check within a predetermined period of time.

In response, the load balancer 320 communicates a predetermined packet to the backup server 340 including a command to deactivate any and all write operation requests at step 327 to activate read only mode. Additionally, and/or alternatively (though not depicted), the load balancer 320 may communicate a predetermined packet to user device 310 to deactivate any and all tasks that include a write request available within the remote EHR system application. In other words, in an embodiment, the load balancer 320 communicates a predetermined data packet that disables any and/or all tasks accessible in the remote EHR system application that include at least one information request that writes (e.g. attempts to write) information to an EHR database cluster. In response to receiving the disabling packet, the backup server 340 deactivates, disables, locks, or otherwise suspends any and/or all write operations at step 344. In other words, in response to receiving the disabling packet from the load balancer 320, the backup server 340 continues to respond to read requests; but, does not respond to write requests.

At step 312, a request for information is communicated from the user device 310 to the load balancer 320. The request may comprise a request to write patient information to a EHR database cluster or read patient information in a EHR database cluster. Upon receipt of the request for information the load balancer 320 may parse the request to determine whether the request includes either a read operation or a write operation. In the event that the information request includes a read request the load balancer 320 may direct the request to the backup server 340 at step 328. In response, the backup server 340 may communicate the information associated with the read request back to the user device 310 at step 345. In some embodiments, the response of the backup server 340 is directly to user device 310. In some embodiments, the response of the backup server 340 to user device 310 is through the load balancer 320. In the event that the information request includes a write operation, the load balancer 320 may communicate a notification to the user device that the EHR system is in a read only status, deny the information request, and/or communicate a predetermined packet to the user device disabling tasks that include write operations to a EHR database cluster at step 329. Thus, some embodiments disclosed herein provide an automatic write protection function for backup EHR systems that allows for, and facilitates, automated backup of a master database cluster including the EHR system application, patient data, facility data, and/or any other data stored within the EHR database cluster.

Figure 4:
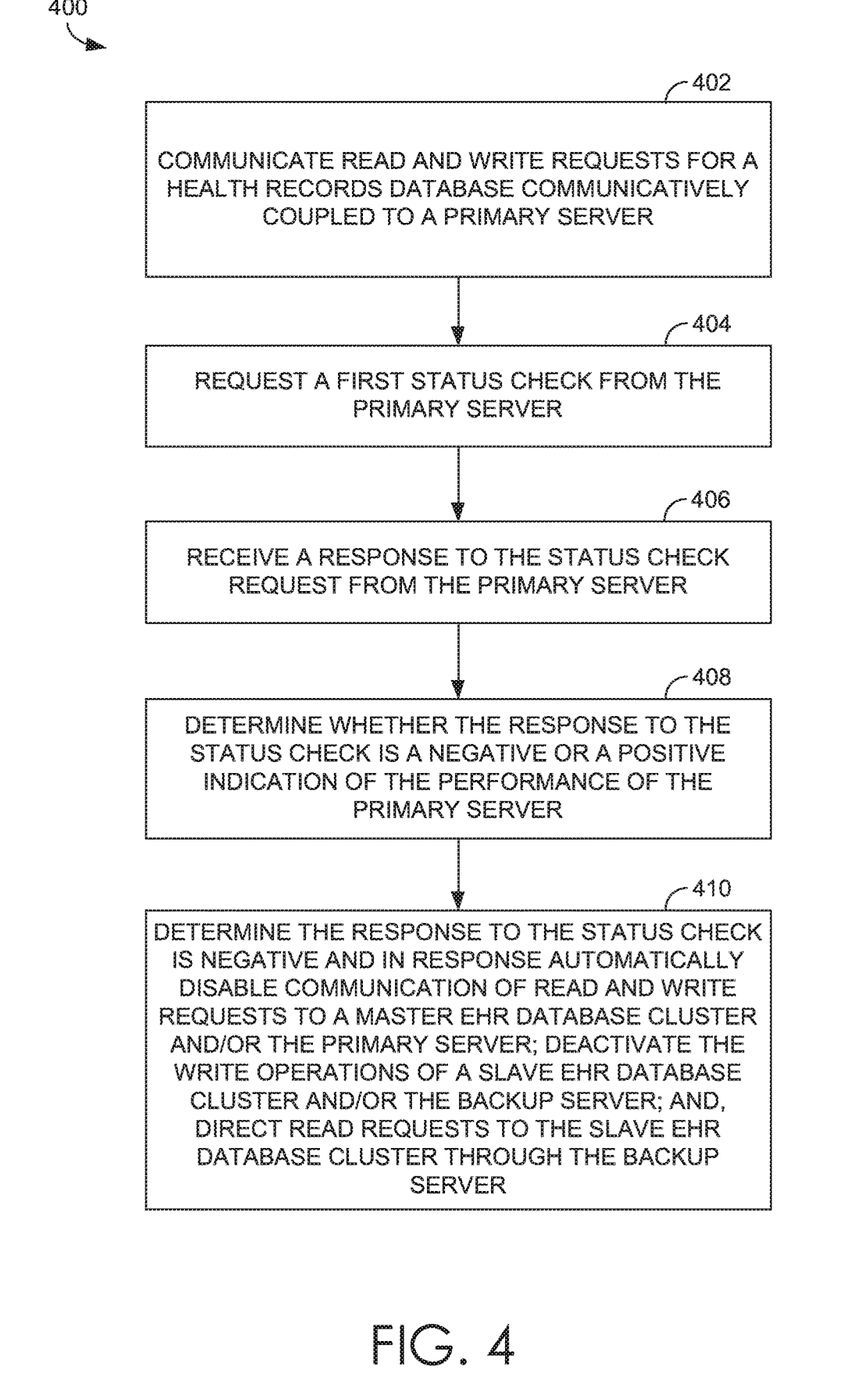
FIG. 4 is a block diagram of an exemplary method suitable to implement embodiments of the present invention.

Turning now to FIG. 4 and with reference to FIG. 2, an exemplary method 400 for automatic medical database preservation is depicted. Generally, method 400 facilitates the automatic backup of EHR records, facility records, and other data stored in a EHR database cluster. Additionally, and/or alternatively, method 400 may facilitate the automatic preservation of an EHR system application. Some embodiments of method 400 are suitable to facilitate the automatic preservation of a server based EHR system, such as depicted in environment 100. Some embodiments of method 400 are implementable with a load balancer system, such as load balancer 106.

Method 400 may begin with the communication of read and write requests for an electronic health records database communicatively coupled to a first server by a load balancer at block 402. Some embodiments of block 402 are facilitated by a load balancer, such as load balancer 106. For instance, a receiver, such as receiver 212, may receive an information request from a user device, such as user device 102, intended for an electronic health records database. The load balancer 106 may detect whether the information request is a write request or a read request. For instance, a request identifier, such as request identifier 214, may parse the information request and determine whether the packet of data associated with the request includes data intended to be written in an EHR database or includes a request for information already present in the EHR database.

In some embodiments, when the request identification component determines that an information request is a write request (e.g. includes at least one write operation) the remote device communicator, such as remote device communicator 210, activates a server communicator, such as server communicator 220, to add the write request to a digital log with a time stamp and an indication of the data record modified by the write request. For instance, the backup manager 222 may store the time stamp and an indication of the data record modified by the write request in memory accessible to the load balancer 106.

At step 404, the load balancer may request a status check from the primary server. Generally, the status check indicates the operational performance of the primary server. For instance the status checker 224 may generate a predetermined packet of data including the destination IP address of the primary server and the response IP address of the load balancer 106. Further the packet may include an additional set of data pre-programmed to trigger the primary server, such as primary server 108, to respond with an indication of the operational performance of the primary server. It will be understood that the set of data pre-programmed to trigger the primary server may vary depending on the specific hardware, communication protocol, operating system, and so on. For instance, the preprogrammed data may comprise computer readable instructions that triggers an automatic database diagnostic monitor (not depicted) running on the primary server to initialize an analysis and validation of all instances of the master EHR databases and EHR system application communicatively coupled with and/or stored in the memory of the primary server.

At step 406, the load balancer may receive a response to the status check request. Generally, the primary server may respond to receiving the predetermined packet of data by initializing a diagnostic process to test the performance or integrity of the primary server and/or the master EHR database cluster accessible to (i.e. communicatively coupled with and/or stored in the memory of) the primary server. For example, an automatic database diagnostic monitor (not depicted) running on a primary server, such as primary server 108, may initialize an analysis and validation of all instances of the master EHR databases and EHR system applications communicatively coupled with and/or stored in the memory of the primary server. Such an analysis may include: identification of CPU bottlenecks; identification of memory structure issues, such as buffer cache size; detecting input/output capacity issues; analysis of structure query language (SQL) (or other relational database programming language) load burden; EHR system application latency; database data integrity testing; etc. The primary server, such as server 108, may communicate the results of the diagnostic process to the load balancer by transmitting a packet of data to a receiver, such as receiver 212, of a load balancer, such as load balancer 106. The remote device communicator 210 may parse the packet of data to determine the IP and/or MAC address of the source of the packet and compare the IP and/or MAC address of the source to the IP and/or MAC address of the primary server and/or backup server. If the addresses match, the remote device communicator 210 may then pass the data to the status checker 224 to analyze the packet of data. The analysis may comprise a comparison of the diagnostic process to a predetermined set of rules stored in the memory of the load balancer 106. It will be understood by those skilled in the art that the rules may vary by the requirements and/or tolerances of the specific database administrator and/or the policies, standards, and procedures of the hospital, healthcare facility, clinic, and so on. However, in general, at least three conclusions may be determined based on the analysis of the diagnostic process: 1) the primary server and the master EHR database cluster is operational; 2) the primary server is operational but the master EHR database cluster is nonoperational; and/or, 3) the primary server is nonoperational. Further, the load balancer may automatically determine that absence of a response from the primary server within a predetermined duration after the load balancer requests the status check is an indication that the first server is nonoperational and/or offline. In some embodiments, step 404 and 406 may be repeated for a backup server, such as backup server 112.

Alternatively, and/or additionally, the primary server may periodically, continuously, and/or intermittently initialize the diagnostic process independent of receipt of the predetermined packet of data. For example, the primary server 108 may be preprogrammed to initialize the automatic database diagnostic monitor at times when the EHR system demand is lowest and/or expected to be at its lowest. This may be done, for example, based on analysis of historical EHR system usage within the hospital, healthcare facility, clinic, and the like. Additionally, and/or alternatively, the primary server may be programmed to initialize the diagnostic process when the EHR system demand is expected to be at its highest. Such a setting, may be desirable in situations where the EHR system was recently updated and stress testing the primary server is needed. In such an embodiment, in response to receiving the predetermined packet of data from the load balancer, the primary server responds with the results of the diagnostic process run most recently. In other words, the primary server may communicate the most recent results of the diagnostic process to the load balancer.

At block 408, the load balancer may determine whether the response to the status check is a negative or a positive indication of the performance of the primary server. For instance, generally where the primary server and the master EHR database cluster are operational, the load balancer may determine that the response to the status check is a positive indication of the performance of the primary server. Additionally, a negative category/indication generally indicates that either the primary server or the master EHR database cluster is nonoperational and/or offline. As stated above, it will be understood by those skilled in the art that the rules may vary by the requirements and/or tolerances of the specific database administrator and/or the policies, standards, and procedures of the hospital, healthcare facility, clinic, and so on.

In some embodiments of block 408, in response to the load balancer determining that the status check is positive, a backup manager, such as backup manager 222, triggers the backup server 112 to back up the master EHR database cluster 110 communicatively coupled to the primary server 108 to the slave EHR database cluster 114 communicatively coupled to the backup server 112. For example, the load balancer, may access a digital log of write requests communicated by the load balancer to the primary server. Based on the digital log of write requests, a set of updated, modified, edited, or otherwise altered health records and/or other data stored in the master EHR database cluster 110 can be identified by the load balancer. The load balancer 106 may send a request for the set of updated health records to the primary server 108. The request may also include the IP and/or MAC address of the backup server 112. In response, the primary server 108 may access the updated health records stored in the master EHR database 110 and communicate the updated health records to the load balancer 106. The load balancer may forward the updated health records set and a command to write the data to the backup server 112 for storage in the slave EHR database cluster 114.

At block 410, the load balancer determines that the status check is negative and, in response, the load balancer 106 automatically disables communication of read and write requests received from the user devices 102 to the master EHR database cluster 110 and/or the primary server 108; deactivates the write operations of the slave EHR database cluster 114 and/or the backup server 112; and, directs read requests intended for the master EHR database cluster 110 to the slave EHR database cluster 114 through the backup server 112. Further, the load balancer may generate a notification indicating deactivation of write operations for visual and/or audio presentation in a graphical user interface of a user device 102 communicatively coupled with the load balancer.

Further, some embodiments of method 400 include reactivation of communication direction to the master EHR database cluster 120 and/or the primary server 108. For example, the load balancer 106 may, at some subsequent point in time, send a status check to the primary server 108 and/or receive a status check from the primary server 108. The load balancer 106 may then determine the status of the primary server 108 and/or the master EHR database cluster 110, similar to step 408. Upon the load balancer 106 determining the status check response is a positive indication of the performance of the primary server 108 and the master EHR database cluster 110, the load balancer 106 may enable communication of read and write requests to master EHR database cluster 110. Further, the load balancer 106 may reactivate write operations of the slave EHR database cluster 114. Additionally, the load balancer 106 may resume directing read and write requests intended for a EHR database to the master EHR database cluster 110 through the primary server 108.

Figure 5:
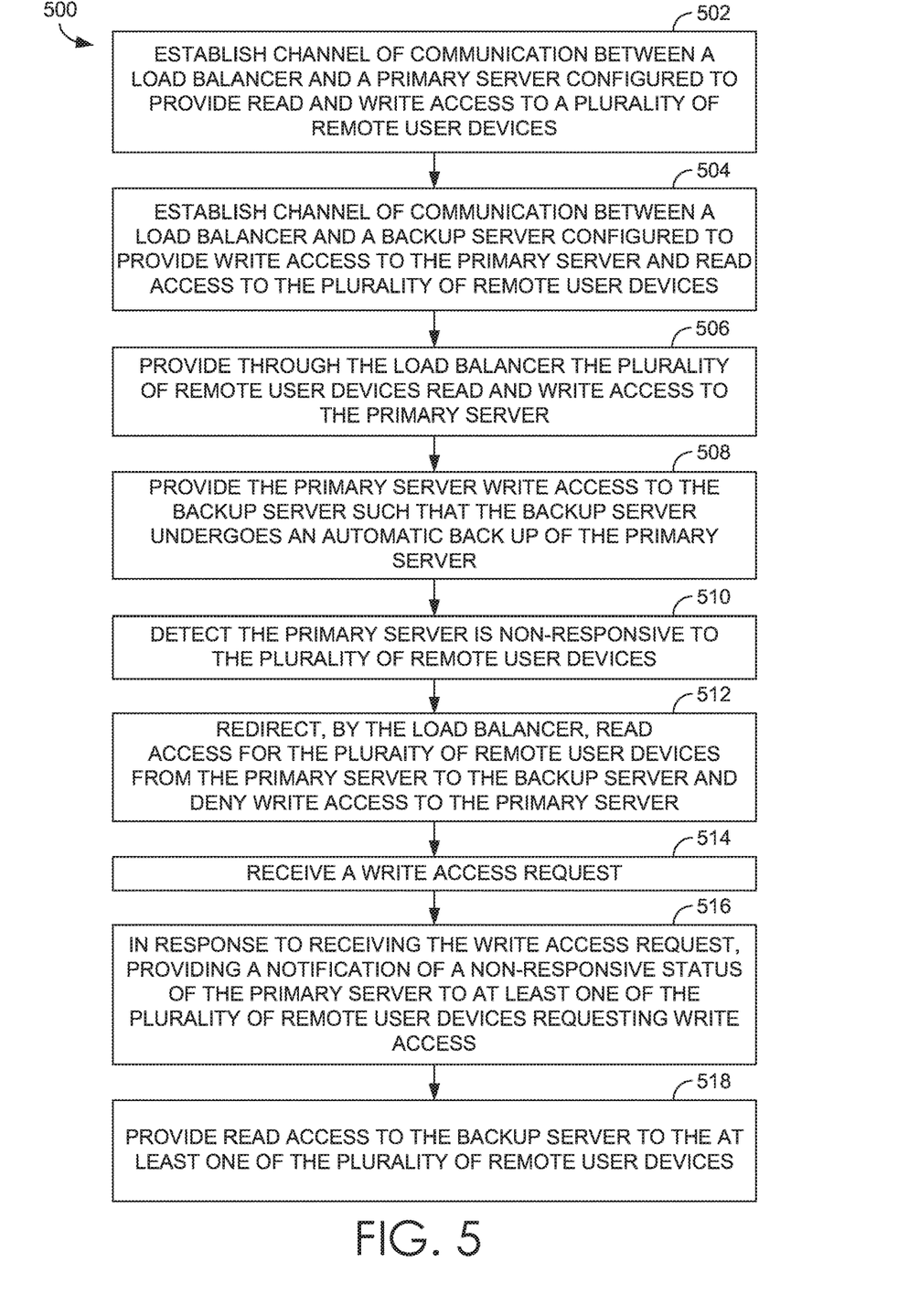
FIG. 5 is block diagram of another exemplary method, in accordance with an embodiment of the present invention.

Turning now to FIG. 5, another exemplary method 500 is depicted for the automatic preservation of a database, such as an EHR database, and/or applications, such as an EHR system application. At block 502, a channel of communication is established between a load balancer, such as load balancer 106, and a primary server, such as primary server 108. The channel of communication is generally configured to provide a plurality of remote user devices read and write access to an EHR database cluster through the load balancer. For instance, a load balancer, such as load balancer 106, may send a packet of information to an IP address associated with the primary server, such as primary server 108. The packet may include further include the IP address of the load balancer. At block 504, a channel of communication is established between a load balancer, such as load balancer 106, and a backup server, such as backup server 112. The channel of communication is generally configured to provide write access to the primary server (directly and/or indirectly) and read access to the plurality of remote user devices. In some embodiments, block 502 and block 504 are performed simultaneously, substantially simultaneously, sequentially, and/or in parallel.

At block 506, the load balancer provides the plurality of remote user devices read and write access to the primary server. The remote user devices, such as user device 102, may communicate read and/or write requests associated with patient information to the load balancer, such as load balancer 106. In an embodiment, the user device 102 may send a packet(s) of data including the read and/or write request to the load balancer. The packet(s) of data may also include an IP and/or MAC address associated with the particular user device. Further, the packet may include the destination IP and/or MAC address associated with the load balancer. Thus, in an embodiment, communications intended to read and/or write information to an EHR database are directed to the load balancer. A receiver, such as receiver 212, may parse the information to identify the source IP address and provide the information to the to a request identifier, such as request identifier 214. The request identifier may determine whether the request is a read or write operation. Based on the status of the primary server and the master EHR database cluster, a transmitter, such as transmitter 216 may transmit the read and/or write request to the primary server.

At block 508, the load balancer provides the primary server write access to the backup server such that the backup server undergoes an automatic back up of the primary server. For example, in an embodiment, each write request a request identifier, such as request identifier 214, identifies is communicated to a backup manager, such as backup manager 222. The backup manager may store, in memory, a digital log of each write request received by the load balancer and communicated to the primary server. Periodically, intermittently, and/or continuously, a server communicator, such as server communicator 220, may access the digital log and generate a list of write requests received by the load balancer since the previous backup. The list may be sent, by the transmitter, to the primary server. In some embodiments, the communication also includes the IP address of a backup server, such as backup server 112. The primary server may identify the data structures (such as EHR patient records, EHR system application(s), and the like) stored in the master EHR database cluster identified by the list of write requests. The primary server may then communicate the data structures directly and/or indirectly to the backup server and/or the slave EHR database cluster.

At block 510, the load balancer detects that the primary server is non-responsive to the plurality of remote user devices. For example, a transmitter, such as transmitter 216, may communicate read and/or write requests to a primary server, such as primary server 108. A remote device communicator, such as remote device communicator 210, may temporarily hold a record of some and/or all of the communications sent to the primary server. For instance, as the transmitter generates the communication packet the destination IP address may be scanned by a status checker, such as status checker 224, and matched to the known IP address of the primary server. A server communicator, such as server communicator 220, may then trigger the remote device communicator to temporarily hold a record of the communication. The remote device communicator may wait for a receiver, such as receiver 212, to receive the response from the primary server associated with the request temporarily held by the remote device communicator. If a response is not receive within a predetermined period of time the remote device communicator may activate the status checker to request a status check from the primary server. Additionally, and/or alternatively, the remote device communicator may determine that a predetermined number of failed requests (requests in which a response is not received within the predetermined time) within a predefined interval automatically activates a switcher, such as switcher 226, to initiate the contingency read only mode protocol.

At block 512, in response to detecting that the primary server is non-responsive to the plurality of remote user devices, the load balancer redirects read access for the plurality of remote user devices from the primary server to the backup server, and denies write access to the primary server. For example, the load balancer 106 may communicate a predetermined packet to user device 102 including a command to deactivate any and/or all tasks that include a write request available within a remote EHR system application operating on the user device 102. In other words, in an embodiment, the load balancer disables any and/or all tasks accessible in the remote EHR system application that include at least one information request that writes (e.g. attempts to write) information to an EHR database cluster. Further, the load balancer 106 may communicate a predetermined disabling packet, to the backup server 112 which deactivates, disables, locks, or otherwise suspends any and/or all write operations. In other words, in response to receiving the disabling packet from the load balancer, the backup server continues to respond to read requests; but, does not respond to write requests. Additionally, a switcher, such as switcher 226, may instruct a transmitter, such as transmitter 216, to communicate read requests received from user device 102 to the IP address associated with the backup server 112.

A write access request is received at block 514. For example, a clinician using a remote EHR system application (e.g. a EHR system client) on a user device, such as user device 102, may attempt to enter a new medication prescription into a patient's EHR record. As part of this attempt, the remote EHR system application may generate a set of write requests and a set of read requests that are ultimately intended for the EHR database cluster. The remote EHR system application and/or the user device may communicate the write request(s) to the IP address associated with a load balancer, such as load balancer 106. The read and write requests may be received by receiver 212. Receiver 212, may parse the request to identify the source address and pass the request to the request identifier 214. The request identifier 214 may parse the request to determine whether the request includes a read operation or a write operation. Returning to the example, the receiver 212, parses the communication and, in this case, identifies a particular user device. The request identifier 214 parses the communication and, in this case, identifies both read and write operations. At block 516, in response to receiving the write access request, the load balancer provides a notification of the non-responsive status of the primary server to the particular user device requesting write access. For instance, remote device communicator 210 may generate a predetermined packet of information including a notification presentable within the remote EHR system application. The receiver 212 may pass the identity of the source of the request to the transmitter 216. The notification may then be communicated to the source (user device 102) of the request by the transmitter 216. The notification may then be presented to the user of the user device within the remote EHR system application. At block 518, the load balancer provides read access to the backup server 112 to the at least one of the plurality of remote user devices requesting access.

From the foregoing, it will be seen that this technology is one well adapted to attain all the ends and objects described above, including other advantages which are obvious or inherent to the structure. It will be understood that certain features and subcombinations are of utility and may be employed without reference to other features and subcombinations. This is contemplated by and is within the scope of the claims. Since many possible embodiments of the described technology may be made without departing from the scope, it is to be understood that all matter described herein or illustrated the accompanying drawings is to be interpreted as illustrative and not in a limiting sense.

What is claimed is:

1. A system comprising:
   a remote access hub that is communicatively coupled to a first server maintaining a first database and a second server maintaining a second database, the first server configured for receiving read and write requests from a plurality of remote user devices via the remote access hub, the second server configured for receiving read and write requests from the first server via the remote access hub and only read requests from the plurality of remote user devices via the remote access hub;
   the remote access hub including computer-readable instructions that when executed by one or more processors of the remote access hub cause the remote access hub to perform operations of:
   receiving a first plurality of requests to access patient information, the plurality of requests including write requests and read requests communicated from a remote user device of the plurality of remote user devices;
   in response to a determination that the first server is online, forwarding the first plurality of requests to the first server;
   receiving a second plurality of requests to access patient information, the second plurality of requests including write requests and read requests communicated from the remote user device of the plurality of remote user devices;
   determining that the first server is offline;
   responsive to the determination that the first server is offline, forwarding only the read requests of the second plurality of requests to the second server; and
   in response to the determination that the first server is offline, transmitting a command to the plurality of remote computing devices disabling activities in an application executed by the plurality of remote computing devices that generates write requests.

2. The system of claim 1, wherein the first database is stored in a first set of computer readable storage media and the second database is stored in a second set of computer readable storage media disparate from the first set of computer readable storage media.

3. The system of claim 1, wherein determining the first server is online comprises communicating a predetermined signal to the first server.

4. The system of claim 3, wherein the first server communicates a backup request to the second server in response to receiving the predetermined signal.

5. The system of claim 3, further comprising receiving a predetermined response from the first server; and
   responsive to the predetermined response, automatically communicating a backup request to the second server.

6. The system of claim 1, further comprising storing each write request of the second plurality of requests in a locally maintained log.

7. The system of claim 6, wherein in response to detecting that the first server is online after detecting that the first server was offline, forwarding a third plurality of requests to the first server, the third plurality of requests including write request and read requests.

8. Non-transitory computer readable media storing computer readable instructions that when provided to at least one processor of a remote access hub, cause the at least one processor to perform actions comprising:
   receiving a first plurality of requests to access patient information, the plurality of requests including write requests and read requests communicated from a remote user device of the plurality of remote user devices;

in response to a determination that the first server is online, forwarding the first plurality of requests to a first server, the first server configured for receiving read and write requests from a plurality of remote user devices;

receiving a second plurality of requests to access patient information, the second plurality of requests including write requests and read requests communicated from the remote user device of the plurality of remote user devices;

determining that the first server is offline; and responsive to the determination that the first server is offline, forwarding only the read requests of the second plurality of requests to a second server and transmitting a command to the plurality of remote user devices disabling activities in an application executed by the remote user devices that generates write requests.

9. The non-transitory computer readable media of claim 8, further comprising-storing each write request of the second plurality of requests in a locally maintained log.

10. The non-transitory computer readable media of claim 8, wherein in response to detecting that the first server is online after detecting that the first server was offline, forwarding a third plurality of requests to the first server, the third plurality of requests including write request and read requests.

11. The non-transitory computer readable media of claim 8, wherein determining the first server is online comprises communicating a predetermined signal to the first server.

12. The non-transitory computer readable media of claim 11, wherein the first server communicates a backup request to the second server in response to receiving the predetermined signal.

13. The non-transitory computer readable media of claim 11, further comprising receiving a predetermined response from the first server; and responsive to the predetermined response communicating a backup request to the second server.

* * * * *

UNITED STATES PATENT AND TRADEMARK OFFICE
CERTIFICATE OF CORRECTION

PATENT NO. : 11,295,836 B2
APPLICATION NO. : 15/856340
DATED : April 5, 2022
INVENTOR(S) : Howard T. Marano, Deepak Kumar Jain and Karthikeyan Sukumaran It is certified that error appears in the above-identified patent and that said Letters Patent is hereby corrected as shown below:

In the Claims

Claim 9, Column 20, Line 2:
The line reading "further comprising-storing each write request of the second" should read -- further comprising storing each write request of the second --.

Signed and Sealed this
Fifteenth Day of November, 2022

Katherine Kelly Vidal
*Director of the United States Patent and Trademark Office*